United States Patent
Kim et al.

(10) Patent No.: US 10,212,399 B2
(45) Date of Patent: Feb. 19, 2019

(54) WEARABLE DEVICE FOR GENERATING IMAGE SIGNAL, AND SYSTEM FOR CONTROLLING SAME

(71) Applicant: NEXSYS CO., LTD., Gyeonggi-do (KR)

(72) Inventors: Donghyun Kim, Kkachimaeul (KR); Myoungsung Kim, Gyeonggi-do (KR); Soyoung Lee, Bokjeong-dong (KR); Yulgon Lee, Inchang-dong (KR); Junheon Lee, Hwayang-dong (KR)

(73) Assignee: NEXSYS CO., LTD., Gyeonggi-do (KR)

( * ) Notice: Subject to any disclaimer, the term of this patent is extended or adjusted under 35 U.S.C. 154(b) by 0 days.

(21) Appl. No.: 15/548,283

(22) PCT Filed: Nov. 13, 2015

(86) PCT No.: PCT/KR2015/012244
§ 371 (c)(1),
(2) Date: Aug. 2, 2017

(87) PCT Pub. No.: WO2016/133269
PCT Pub. Date: Aug. 25, 2016

(65) Prior Publication Data
US 2018/0020194 A1   Jan. 18, 2018

(30) Foreign Application Priority Data

Feb. 16, 2015  (KR) .................. 10-2015-0023073
Mar. 31, 2015  (KR) .................. 10-2015-0045080

(51) Int. Cl.
*H04N 7/18*   (2006.01)
*G08B 21/02*  (2006.01)
(Continued)

(52) U.S. Cl.
CPC ............ *H04N 7/188* (2013.01); *A42B 3/042* (2013.01); *A42B 3/0433* (2013.01); *A42B 3/30* (2013.01);
(Continued)

(58) Field of Classification Search
CPC ...................................... H04N 7/188
(Continued)

(56) References Cited

U.S. PATENT DOCUMENTS 6,121,881 A     9/2000  Bieback
9,398,007 B1 *  7/2016  Wegener ............... H04W 12/06
(Continued)

FOREIGN PATENT DOCUMENTS

JP   2003-516831 A   5/2003
JP   2004102750 A    4/2004
(Continued)

OTHER PUBLICATIONS

International Search Report mailed in corresponding International Patent Application No. PCT/KR2015/012244 dated Mar. 14, 2016, consisting of 5 pp. (English Translation Provided).
(Continued)

*Primary Examiner* — Leron Beck
(74) *Attorney, Agent, or Firm* — Volpe and Koenig, P.C.

(57) ABSTRACT

An wearable device and a system for controlling the same are provided. The wearable device is connected to a user biometric state measurement device to capture an image of a certain place or situation, and the system remotely controls the wearable device and the user biometric state measurement device in real time.

19 Claims, 8 Drawing Sheets

(51) Int. Cl.
  G08B 21/18    (2006.01)
  G08B 25/10    (2006.01)
  G08B 25/14    (2006.01)
  H04W 4/02     (2018.01)
  A42B 3/04     (2006.01)
  A42B 3/30     (2006.01)
  A61B 5/0205   (2006.01)
  A61B 5/00     (2006.01)
  G08B 21/04    (2006.01)
  H04B 1/3827   (2015.01)
  H04N 1/00     (2006.01)
  G08B 25/01    (2006.01)
  A61B 5/024    (2006.01)
  A61B 5/11     (2006.01)
  A61B 5/145    (2006.01)

(52) U.S. Cl.
  CPC ......... *A61B 5/02055* (2013.01); *A61B 5/441* (2013.01); *A61B 5/6803* (2013.01); *G08B 21/02* (2013.01); *G08B 21/0453* (2013.01); *G08B 21/18* (2013.01); *G08B 25/016* (2013.01); *G08B 25/10* (2013.01); *G08B 25/14* (2013.01); *H04B 1/385* (2013.01); *H04N 1/00106* (2013.01); *H04N 7/185* (2013.01); *H04W 4/02* (2013.01); *A61B 5/02438* (2013.01); *A61B 5/1112* (2013.01); *A61B 5/14542* (2013.01); *A61B 2560/0247* (2013.01); *H04B 2001/3866* (2013.01); *H04N 2201/0084* (2013.01)

(58) Field of Classification Search
  USPC ...................................................... 348/158
  See application file for complete search history.

(56) References Cited

U.S. PATENT DOCUMENTS

| | | | |
|---|---|---|---|
| 9,794,475 B1 * | 10/2017 | Tome | H04N 1/00129 |
| 2002/0190866 A1 | 12/2002 | Richardson | |
| 2006/0293892 A1 * | 12/2006 | Pathuel | G06F 21/32 |
| | | | 704/246 |
| 2009/0174547 A1 | 7/2009 | Greene | |
| 2011/0112418 A1 | 5/2011 | Field | |
| 2012/0212339 A1 | 8/2012 | Goldblatt | |
| 2014/0172132 A1 | 6/2014 | Ura | |
| 2014/0270200 A1 * | 9/2014 | Usher | H04R 1/1041 |
| | | | 381/57 |
| 2014/0364212 A1 * | 12/2014 | Osman | A63F 13/213 |
| | | | 463/31 |
| 2014/0368658 A1 | 12/2014 | Costa | |
| 2016/0022144 A1 * | 1/2016 | Hansen | H04W 4/008 |
| | | | 340/870.3 |
| 2016/0189450 A1 * | 6/2016 | Anderson | G06K 19/07381 |
| | | | 340/5.51 |

FOREIGN PATENT DOCUMENTS

| | | |
|---|---|---|
| JP | 2006-239197 A | 9/2006 |
| JP | 2008-043702 A | 2/2008 |
| JP | 2008-047097 A | 2/2008 |
| JP | 2008-203985 A | 9/2008 |
| JP | 2011-513020 A | 4/2011 |
| JP | 2012-058993 A | 3/2012 |
| JP | 2014-117551 A | 6/2014 |
| KR | 10-2012-0094590 A | 8/2012 |
| KR | 10-2012-0104091 A | 9/2012 |
| KR | 10-2012-0138313 A | 12/2012 |
| KR | 10-1454237 B1 | 10/2014 |
| KR | 101489896 B1 | 2/2015 |
| KR | 10-2015-0029486 A | 3/2015 |
| WO | 2016144952 A1 | 9/2016 |

OTHER PUBLICATIONS

Written Opinion mailed in corresponding International Patent Application No. PCT/KR2015/012244 dated Mar. 14, 2016, consisting of 5 pp.

Extended European Search Report issued in corresponding European Patent Application No. 15882802.0 dated Jan. 30, 2018, consisting of 9 pp.

Office Action issued in corresponding Japanese Patent Application No. 2017-543356 dated Sep. 5, 2018, consisting of 5 pages.

* cited by examiner

2000

WEARABLE DEVICE FOR GENERATING IMAGE SIGNAL, AND SYSTEM FOR CONTROLLING SAME

TECHNICAL FIELD

The present disclosure relates to a wearable device for generating an image signal, and a system for controlling the same, and more particularly, to a wearable device connected to a user biometric state measurement device to capture an image of a certain place or situation, and a system for remotely controlling the wearable device and the user biometric state measurement device in real time.

BACKGROUND ART

Recently, wearable devices have emerged. Wearable devices have generally appeared in the form of glasses connected to smartphones or as bands worn on the wrist and, in recent years, have also been able to operate independently of smartphones.

Further, as the wearable device-related technology has been developed, wearable devices may be implemented to have other shapes, such as a helmet worn on the head, in addition to glasses or a band worn on the wrist.

Meanwhile, when an accident such as a fire or an injury in a remote area occurs, in the case of an affected person waiting for rescue or a rescuer about to enter the scene of the accident to aid the affected person, accurate judgment regarding the current status of the event having caused the accident or risks which will be faced by rescuers, as well as the current status of the affected person, may be required to prevent further damage from occurring and to allow the affected person to be safely rescued.

For example, when a fire has occurred in the middle stories of a building consisting of a plurality of stories, in order for a person removed from the scene of the fire by a certain distance to save another person in danger in the fire scene, the person needs to judge a situation at the scene of the fire accurately to determine a safe, quick rescue method, and may determine the current state of the person at the scene of the fire accurately to determine a precise rescue time.

In general, a person distant from an endangered person may use cell phones or radios to receive information on the surroundings or physical condition of the endangered person. However, these methods are difficult to use in the case that urgent rescue is required in the above-mentioned fire or injury situation, as well as in the case that it is impossible to perform remote communications or perform communications in real time, or if it is only possible to transmit information regarding the situation with audio or visual data. Thus, it may be difficult to accurately send information on the surroundings or physical condition of an endangered person to others over a long distance.

As a concrete example of such a situation, accidents occurred because, when rescuers entered the World Trade Tower in the September 11 terrorist attacks and rescued people in the accident situation, accurate information regarding the situation at the site and the current status of endangered persons was not sent to a rescue center, such that the rescuers, as well as people at the site of the accident, were in danger, or died.

As described above, events and accidents continue to occur around us. In addition, even though information regarding the physical condition or surroundings of endangered persons needs to be frequently sent to others in a remote location, a technology for a person distant from an endangered person to accurately determine the situation in the surroundings or physical condition of endangered persons does not exist.

Thus, as a method for solving such a problem, a need exists for a means for enabling a person in a predetermined environment to accurately transmit his or her situation or physical condition to a person at a distant location using images. On the other hand, there is a demand for a means for enabling a person at a distant location to free a specific person from a predetermined environment or to accurately confirm information on the surroundings or physical condition of the specific person in order to aid the specific person.

DISCLOSURE

Technical Problem

An aspect of the present disclosure may provide a biometric state measurement device which may accurately measure the current state of a user by detecting a user biometric signal to solve the above-mentioned problem.

Another aspect of the present disclosure may provide a wearable device which may capture an image and perform wireless communications, based on a user biometric signal measured by a biometric state measurement device, to solve the above-mentioned problem.

Another aspect of the present disclosure may provide a system which may monitor a user in a remote location in real time by collectively controlling the wearable device and the biometric state measurement device to solve the above-mentioned problem.

Another aspect of the present disclosure may provide a system which may detect a specific individual's biometric signal using the biometric state measurement device, may capture an image of the specific individual's surroundings, based on the measured biometric signal, and may transmit the measured biometric signal and the captured image to a person in a remote location, to solve the above-mentioned problem by allowing monitoring of the specific individual by the person in the remote location.

Technical tasks obtainable from the present disclosure may be not limited to the above-mentioned technical tasks. Other unmentioned technical tasks can be clearly understood from the following description by those of ordinary skill in the technical field to which the present disclosure pertains.

Technical Solution

According to an aspect of the present disclosure, a wearable device generating a user surroundings image signal in a wireless communications system may include: a frame unit worn on the body of a user; an image pick-up unit capturing a user surroundings image; a battery unit supplying power to the wearable device; a Long-Term Evolution (LTE) communications module embedded in the wearable device, and directly connected to at least one external device to transmit and receive a communications signal; a voice signal input/output unit receiving a voice signal to be transmitted to the at least one external device from the user, or outputting a voice signal received from the at least one external device to the user; and a control unit controlling the image pick-up unit such that the image pick-up unit may capture the user surroundings image in response to a first command received from a biometric state measurement device, the control unit generating a user surroundings image signal including the captured user surroundings image and transmitting the generated user surroundings image signal to the at least one external device through the LTE communications module. When a value, represented by user biometric signal information measured by the biometric state measurement device, differs from a predetermined reference value by an amount equal to the predetermined value or more, the first command may be transmitted from the biometric state measurement device.

The frame unit may be a helmet wearable on the head of the user.

The biometric state measurement device may be worn on the body of the user wearing the helmet to measure at least one type of biometric signal information among user heart rate, user body temperature, user skin condition, user body oxygen amount, user surroundings nitrogen amount, user surroundings carbon monoxide amount, and user surroundings ultraviolet light change.

The transmitting of a signal to the at least one external device may include directly transmitting a signal to the at least one external device through the LTE communications module, or transmitting a signal to the at least one external device through a relay station within a predetermined radius of the user.

The first command may include the user biometric signal information measured by the biometric state measurement device, and when the value, represented by the measured user biometric signal information, differs from the predetermined reference value by an amount equal to the predetermined value or more, the first command may be transmitted from the biometric state measurement device to the wearable device and the at least one external device, respectively.

The first command may include the user biometric signal information measured by the biometric state measurement device, and the first command may receive existing biometric signal result information of the user from the at least one external device, may compare a value, represented by the received existing biometric signal result information of the user, with the value, represented by the measured user biometric signal information, and when the value, represented by the measured user biometric signal information, differs from the value, represented by the received existing biometric signal result information, by an amount equal to the predetermined value or more, may be transmitted from the biometric state measurement device to the wearable device and the at least one external device, respectively.

The battery unit may include any one of a lithium-ion battery, a lithium-ion polymer battery, or a lithium iron phosphate (LiFePo4) battery.

The wearable device generating a user surroundings image signal in a wireless communications system may further include a position measurement unit performing position measurement using global positioning system (GPS) or Bluetooth® low energy (BLE). The control unit may control the position measurement unit such that the position measurement unit may measure a position of the user so as to generate user position measurement information.

The wearable device generating a user surroundings image signal in a wireless communications system may further include a memory unit storing the generated user surroundings image signal and the generated user position measurement information. The control unit may control storing the user surroundings image signal and the user position measurement information in the memory unit, or transmitting the user surroundings image signal and the user position measurement information to the at least one external device.

The wearable device generating a user surroundings image signal in a wireless communications system may further include a user input unit enabling the user to enter a control command. The control unit may control, in response to a second command entered through the user input unit, at least one of capturing a user surroundings image by the image pick-up unit, measuring a position of the user by the position measurement unit, storing the user surroundings image signal and the user position measurement information in the memory unit, and transmitting the user surroundings image signal and the user position measurement information to the at least one external device.

According to an aspect of the present disclosure, a device for measuring a user biometric signal in a wireless communications system may include: a frame unit worn on the body of a user; a biometric signal measurement unit sensing a user biometric signal an LTE communications module embedded in the device, and directly connected to at least one external device to transmit and receive a communications signal; and a control unit determining a user biometric state by determining whether a value, represented by the sensed user biometric signal, differs from a predetermined reference value by an amount equal to the predetermined value or more. When a biometric state result is determined as the value, represented by the sensed user biometric signal, differing from the predetermined reference value by an amount equal to the predetermined value or more, the control unit may control generating an alarm signal including the sensed user biometric signal and transmitting the generated alarm signal to a remote monitoring server through the LTE communications module, and the control unit may transmits the generated alarm signal to an image signal generation device. The alarm signal, transmitted to the image signal generation device, may further include image capturing instruction information for instructing the image signal generation device to capture a user surroundings image.

According to an aspect of the present disclosure, a system for remotely monitoring a physical condition using a wireless communications network may include: an image signal generation device; a biometric signal measurement device; and a remote monitoring server. When as a sensing result of a user biometric signal, a biometric state result is determined as a value, represented by the sensed user biometric signal, differing from a predetermined reference value by an amount equal to the predetermined value or more, the biometric signal measurement device may generate an alarm signal including the sensed user biometric signal and may transmit the generated alarm signal to the remote monitoring server and the image signal generation device through an LTE communications module included in the biometric signal measurement device. The alarm signal, transmitted to the image signal generation device, may further include image capturing instruction information for instructing the image signal generation device to capture a user surroundings image. The remote monitoring server may be directly connected to the LTE communications module included in the biometric signal measurement device to receive the alarm signal including the user biometric signal, may be directly connected to an LTE communications module included in the image signal generation device to receive an image signal including an image captured by the image signal generation device, and may perform at least one of outputting the received captured image through a display unit or storing the received captured image in a memory.

The remote monitoring server may be any one of a personal computer (PC) or a user equipment (UE).

The remote monitoring server may transmit, to the image signal generation device, an image quality control message for instructing the image signal generation device to capture an image having image quality of a predetermined standard or higher, and in response to the image quality control message, may receive, from the image signal generation device, a captured image having the image quality of the predetermined standard or higher.

The remote monitoring server may remotely connect to the biometric signal measurement device and the image signal generation device through the wireless communications network to control operations of the biometric signal measurement device and the image signal generation device.

The remote monitoring server may divide and store, by users, the biometric signal, received from the biometric signal measurement device, and the captured image, received from the image signal generation device, and may output the divided and stored biometric signal and captured image through a display according to previous division methods.

The biometric signal measurement device and the image signal generation device may be wearable devices able to measure a position of a user using a camera, GPS, and BLE, and the biometric signal measurement device and the image signal generation device may transmit the measured user position information to the remote monitoring server, and may receive, from the remote monitoring server, information on a route along which the user is required to move, based on the measured user position information.

When receiving the image quality control message for instructing the image signal generation device to capture the image having the image quality of the predetermined standard or higher, the image signal generation device may capture an image, based on the image quality control message.

When a sensor included in the biometric signal measurement device includes a plurality of sensors, the system may compare a biometric signal value, measured by at least one of the plurality of sensors, with the predetermined reference value, so as to determine whether the measured biometric signal value differs from the predetermined reference value by an amount equal to the predetermined value or more.

Advantageous Effects

According to an exemplary embodiment in the present disclosure, various effects may be provided as follows.

First, an affected individual in a dangerous accident site or an individual working at the site may accurately provide surroundings information and the current state information of the affected individual to an individual located distantly from the accident site, thus providing information regarding the situation at the accident site and the condition of the affected individual.

Second, surroundings information and the current state information of a person easily exposed to danger, such as a low-grade elementary school student or an elderly person, may be provided to protect the person more thoroughly.

Third, an individual in a remote location may control a wearable device worn by an affected individual, such that surroundings and information regarding the current state of the affected individual may be provided to the individual in the remote location, thus increasing accessibility to the affected individual with respect to the individual in the remote location.

It will be appreciated by those of ordinary skill in the art that the effects that could be achieved with the present disclosure are not limited to what has been particularly described hereinabove and other advantages of the present disclosure will be more clearly understood from the following detailed description.

DESCRIPTION OF DRAWINGS

The accompanying drawings, which are included to provide a further understanding of the present disclosure and are incorporated in and constitute part of this application, illustrate embodiment(s) of the invention, and together with the description, serve to illustrate the principle of the present disclosure.

BEST MODE FOR INVENTION

Figure 1:
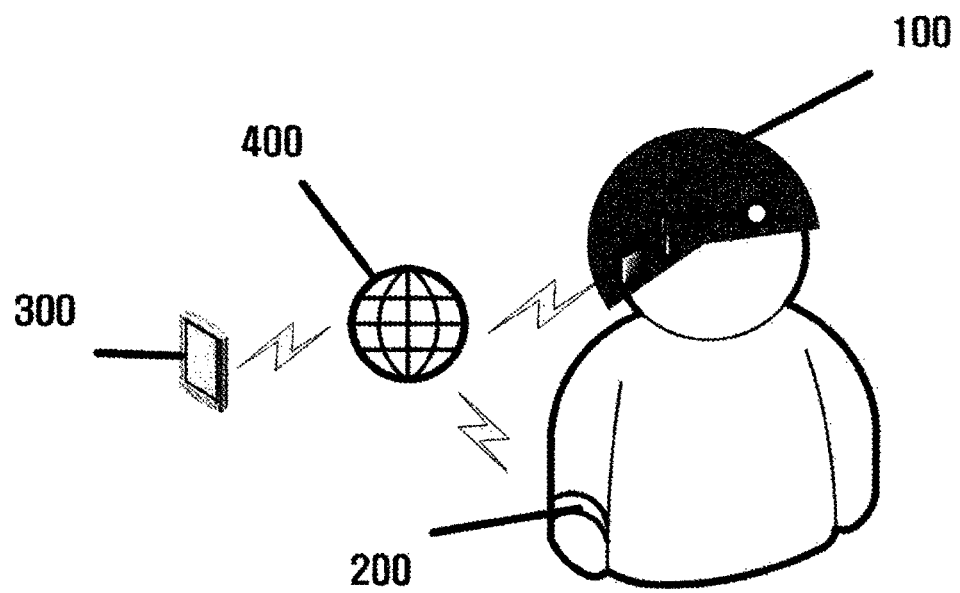
FIG. 1 is a diagram illustrating a system remotely monitoring a biometric state measurement device and a wearable device generating an image signal to which an exemplary embodiment in the present disclosure may be applied.

Exemplary embodiments in the present disclosure will be described hereinafter in detail with reference to the accompanying drawings. The detailed description, which will be given below with reference to the accompanying drawings, is intended to explain exemplary embodiments in the present disclosure, rather than to only illustrate embodiments that can be implemented according to the present disclosure.

Rather, these embodiments are provided so that this disclosure will be thorough and complete and will fully convey the concept of the invention to those of ordinary skill in the art, and the present disclosure will only be defined by the appended claims.

In some cases, to prevent the concept of the exemplary embodiment from being ambiguous, structures and apparatuses of the known art will be omitted, or will be shown in the form of a block diagram based on main functions of each structure and apparatus. The same reference numerals will be used throughout to designate the same or like elements.

When it is said that a part "comprises" or "includes" a component through the specification, this means that unless otherwise specified, the part may further include another component, not excluding another component.

In addition, the term "unit" signifies a unit of processing at least one function or operation. This may be implemented in hardware, software, or any combination thereof. Further, "a" or "an", "one", and their similar terms may include both singular and plural expressions, unless otherwise specified or clearly indicated in the context of the exemplary embodiments.

Specific terms used in the exemplary embodiments in the present disclosure are provided to assist in understanding the present invention, and all terms used herein including technical or scientific terms have the same meaning as those generally understood by those of ordinary skill in the art to which the present disclosure pertains. Various modifications may be made in the specific terms within the range that they do not depart from technical spirits of the present disclosure.

Although terms such as "first" and/or "second" in this specification may be used to describe various elements, it is to be understood that the elements are not limited by such terms. The terms may be used to identify one element from another element. For example, a first element may be referred to as a second element, and vice versa within the range that does not depart from the scope of the present disclosure.

FIG. 1 is a diagram illustrating a system remotely monitoring a biometric state measurement device and a wearable device generating an image signal to which an exemplary embodiment in the present disclosure may be applied.

Referring to FIG. 1, the system remotely monitoring the biometric state measurement device and the wearable device generating an image signal to which the exemplary embodiment in the present disclosure may be applied may include a wearable device 100 generating an image signal (hereinafter referred to as an "image signal generation device"), a biometric state measurement device 200, a server 300 (or a remote monitoring device), and a network 400. FIG. 1 illustrates the system including the image signal generation device 100, the biometric state measurement device 200, the server 300, and the network 400, for easy of description. However, the system may also include at least one image signal generation device 100, at least one biometric state measurement device 200, at least one server 300, and/or at least one network 400.

In an exemplary embodiment in the present disclosure, each of the image signal generation device 100 and the biometric state measurement device 200 may be an Internet of Thing (IoT) device, an object sharing information through wired and wireless networks. Furthermore, the image signal generation device 100 and the biometric state measurement device 200 may be implemented as a wearable device, wearable glasses, a wearable band, a user equipment (UE), a terminal, a mobile station (MS), a mobile subscriber station (MSS), a subscriber station (SS), an advance mobile station (AMS), a wireless terminal (WT), a machine-type communication (MTC) device, a machine-to-machine (M2M) device, or a device-to-device (D2D) device, or may be collectively referred to as "mobile devices".

In addition, in an exemplary embodiment in the present disclosure, the server 300 may be a set of devices, directly communicating with the image signal generation device 100 and the biometric state measurement device 200. According to an exemplary embodiment in the present disclosure, the server 300 may be implemented as a server, a personal computer (PC) or a UE, or the term "server" may be replaced with another term. Furthermore, the server 300 may be collectively referred to as a "mobile or fixed device", such as a desktop PC, a laptop PC, a tablet PC, a smartphone, a Wi-Fi phone, an Internet protocol (IP) phone, an access point (AP), a home gateway (HGW), a set-top box (STB), a PC, a mobile phone, a cellular phone, a personal communication service (PCS) phone, a global system for mobile communications (GSM) phone, a wideband code division multiple access (WCDMA) phone, a mobile broadband system (MBS) phone, a personal digital assistant (PDA), a portable multimedia player (PMP), or the like. Here, the term "mobile device" or "fixed device" may be replaced with the term "PC" or "UE".

Of course, this is only an example, and the present invention may be interpreted as including all devices enabling communications, currently commercialized or those which will be developed in the future, other than the above-mentioned example.

A communication means between the server 300, and the image signal generation device 100 and the biometric state measurement device 200 may include both a short-range communications module, and a wireless communications means using radio waves or infrared light, and all wireless communications means which may be developed in the future may be used.

The network 400 may include a short- or long-range wireless communications module, and may refer to a means that may transmit data or a signal among the image signal generation device 100, the biometric state measurement device 200, and the server 300.

For example, the short-range wireless communications module may refer to a module for short-range wireless communications among the image signal generation device 100, the biometric state measurement device 200, and the server 300. Bluetooth®, radio frequency identification (RFID), infrared data association (IrDA), ultra-wide band (UWB), Zigbee®, or the like may be used as a short-range wireless communications technology.

The long-range wireless communications module, that is, a wireless communications means, may be an IP network, providing a large data transmission and reception service and a seamless data service through an IP, or an all IP network, an IP network structure integrating different networks, based on an IP network, and may include at least one of a wired network, a wireless broadband (WiBro) network, a mobile communications network including a WCDMA network, a mobile communications network including a high speed downlink packet access (HSDPA) network and an LTE network, a mobile communications network including an long-term evolution-advanced (LTE-A) network, a satellite communications network, and a Wi-Fi network.

Figure 2:
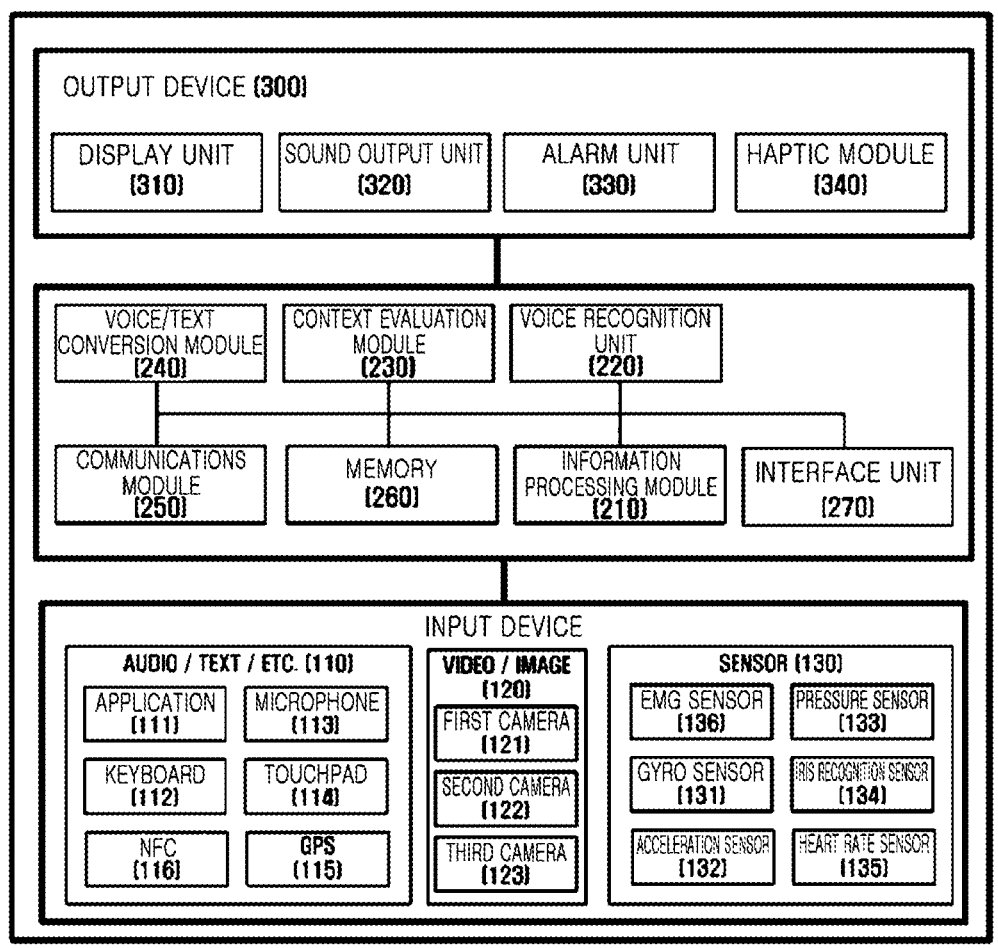
FIG. 2 is a block diagram of a wearable device to which an exemplary embodiment in the present disclosure may be applied.

FIG. 2 is a block diagram of a wearable device to which an exemplary embodiment in the present disclosure may be applied.

Referring to FIG. 2, a wearable device 100 to which the exemplary embodiment in the present disclosure may be applied may include a camera unit 120, a voice input unit 113, a user input unit 112, 114, a sensing unit 130, an output device 300, a wireless communications unit 250 (a communications module), a memory 260, an interface unit 270, a control unit 210, a context evaluation module 230, a voice recognition unit 220, and a power supply unit.

The camera unit 120 may be provided to input a video signal or an image signal, and two or more camera units 120 may also be provided, depending on the configuration of the wearable device. The camera unit 120 may process an image frame, such as a still image or a video, obtained by an image sensor in a video call mode or an image pick-up mode. The processed image frame may be displayed on a display unit 310. Further, the image frame, processed by the camera unit 120, may be stored in the memory 260 or transmitted to an external device through the wireless communications unit 250 (the communications module). Further, when the image signal or the video signal is used as an input for information processing, the camera unit 120 may transmit the image signal or the video signal to the control unit 210.

The voice input unit 113 may be provided to input a voice signal, and may include a microphone or the like. The microphone may receive an external audio signal in a call mode, a recording mode, or a voice recognition mode to process the external audio signal into electrical voice data. The processed voice data may be converted into a transmissible format and may be output to a mobile communications base station through a mobile communications unit in the call mode. The microphone may use various types of noise removal algorithms for removing noise generated when receiving the external audio signal.

The user input unit 112, 114 may generate key input data that a user enters to control operations of the wearable device. The user input unit 112, 114 may include a keypad, a keyboard, a dome switch, a capacitive or resistive touch-pad, a jog wheel, a jog switch, or a finger mouse. In particular, when the touchpad forms a layer structure together with the display unit 310 to be described later, this may be referred to as a "touchscreen".

The sensing unit 130 (a sensor) may sense the current state of the wearable device, such as an open and closed state of the wearable device, a location of the wearable device, or the presence or absence of a contact by the user with the wearable device, to generate a sensing signal for controlling operations of the wearable device. Further, the sensing unit 130 may function as an input unit, receiving an input signal for information processing performed by the wearable device, and may perform various sensing functions, such as recognizing whether the external device connects to the wearable device.

The sensing unit 130 may include a gyro sensor 131, an acceleration sensor 132, a pressure sensor 133, an iris recognition sensor 134, a heart rate sensor 135, and an electromyogram (EMG) sensor 136, and may also include types of sensors currently developed or commercialized and sensors to be developed in the future, such as a skin temperature sensor, a skin resistance sensor, an electrocardiogram (ECG) sensor, an ultraviolet (UV) sensor, a body oxygen sensor, a motion sensor, a fingerprint recognition sensor, a proximity sensor, a nitrogen sensor, and a carbon monoxide sensor.

The pressure sensor 133 may detect whether pressure is applied to the wearable device, the magnitude of the applied pressure, or the like. The pressure sensor 133 may be provided in a portion of the wearable device in which pressure detection is required, depending on a service environment. When the pressure sensor 133 is installed in the display unit 310, a touch input through the display unit 310 and a pressure touch input at which pressure higher than that of the touch input is applied to the display unit 310 may be identified according to a signal output from the pressure sensor 133. Further, according to the signal output from the pressure sensor 133, the magnitude of pressure applied to the display unit 310 at the pressure touch input may be identified.

The motion sensor may include at least one of the gyro sensor 131, the acceleration sensor 132, and a geomagnetic sensor, and may sense a location or movement of the wearable device using the at least one sensor. The acceleration sensor 132 usable in the motion sensor may be a device, converting a change in acceleration in a direction thereof into an electrical signal, and may be widely used with the development of micro-electro-mechanical systems (MEMS) technology. The acceleration sensor 132 may include a gravity sensor, identifying a change in gravitational acceleration. When used with a Bluetooth® v. 4.0 or higher Bluetooth® low energy (BLE)-based beacon, such as v. 4.2, capable of active sensing, the acceleration sensor 132 may identify whether the user passes a specific location and move on the specific location at a moving speed, thus measuring an accurate time in relation to the moving speed. Further, the gyro sensor 131 may measure an angular speed, and may sense a turning direction with respect to a reference direction.

The iris recognition sensor 134 may function to recognize a person using iris information of eyeballs having characteristics inherent to each person. The human iris is completely formed in the 18 months after birth. Once formed, the round iris pattern protruding close to the medial side of the iris rarely changes, and also has a unique shape in every person. Thus, iris recognition may be the application of different iris characteristics computerized for each person to security authentication technology. That is, iris recognition is an authentication method developed as a means of identifying a person by analyzing the shape and color of iris, the morphology of retinal capillaries, or the like, of the person.

The iris recognition sensor 134 may encode an iris pattern, convert an iris code into an image signal, and compare and determine the image signal. The general working principle is as follows. First, when the user's eyes are focused on a mirror in the center of an iris recognizer at a predetermined distance, an infrared camera may be focused using a zoom lens. Subsequently, an iris camera images the user's irises, an iris recognition algorithm may analyze a contrast pattern of the irises by area to generate an iris code unique to an individual. Finally, a comparison and search process may be performed while registering the iris code in a database.

The heart rate sensor 135 may detect a change in photoplethysmogram (PPG), according to a change of a blood vessel thickness, caused by a heartbeat, in order to collect an emotional signal. Furthermore, the heart rate sensor 135 may measure a heart rate per unit time, a heart rate change. When measuring the heart rate per unit time, the heart rate sensor may also measure the heart rate in consideration of a state of surroundings and a state of an object to be measured.

The skin temperature sensor (a body temperature sensor) may include a skin condition sensor, and may measure a skin temperature, according to a change in a resistance value, in response to a change in an ambient temperature, as well as measure a body temperature. The skin temperature sensor may also measure an abnormal rise or fall in the skin temperature, based on a predetermined value, for example, a normal skin temperature of 36.5° C. to 37.5° C. Further, the skin resistance sensor may measure electrical resistance from skin to be used for the skin temperature sensor to measure the skin temperature, according to the change in the resistance value, in response to the change in the ambient temperature.

The UV sensor may detect ultraviolet light, and when a fire has occurred, the UV sensor may detect the fire. For example, when smoke is generated by a fire to block light received by the UV sensor, the amount of UV light that may be detected by the UV sensor may be changed, and thus the UV sensor may measure the changed amount of UV light to sense whether a fire has occurred.

Further, when smoke generated by a fire blocks light illuminated by the UV sensor to a particular place, the UV sensor may detect or determine whether a fire has occurred and the size of the fire, according to an extent that the light is blocked, and may also calculate a saturation of the smoke per unit area, based on the size of the fire determined through the UV light analysis or processing described above.

The body oxygen sensor may measure the amount of oxygen present in the human body, and may refer to a sensor that when the human body in an average condition has the amount of oxygen within a normal range, previously determines various conditions, for example, such as body temperature, ambient temperature, and heart rate, determines the amount of oxygen present in the human body in consideration of changes in the various conditions, and measures the determination result.

The proximity sensor may detect an approaching object, or the presence or absence of an adjacent object, without mechanical contact therewith. The proximity sensor may detect the adjacent object using a change in an alternating current (AC) magnetic field or in a static magnetic field, or using a change rate of capacitance. Two or more proximity sensors may be provided according to configuration types.

The carbon monoxide sensor may measure the concentration of carbon dioxide gas present in the adjacent air, and may use a method of optically measuring the concentration of carbon dioxide using non-dispersive infrared (NDIR) or a method of electrochemically measuring the concentration of carbon dioxide using a solid electrolyte.

The nitrogen sensor may measure the concentration of a nitrogen oxide present in the adjacent air, such as nitrogen monoxide (NO), nitrogen dioxide ($NO_2$), dinitrogen trioxide ($N_2O_3$) or nitrous oxide ($N_2O$), and may use a method using equilibrium potential, a method using current, a method using a conversion cell that converts nitrogen oxide gas into other gas form, or a method using an oxygen-ion conductive solid electrolyte and an electrical signal.

The output device 300 may output an audio signal, a video signal, or an alarm signal. The output device 300 may include the display unit 310, an audio output module, an alarm unit 330, and a haptic module 340.

The display unit 310 may display information processed by the wearable device. For example, when the wearable device is in the call mode, the display unit 310 may display a user interface (UI) or a graphical user interface (GUI). When the wearable device is in the video call mode or the image pick-up mode, the display unit 310 may display captured and received images respectively or simultaneously, and may display the UI or GUI.

Meanwhile, as described above, when the display unit 310 and the touchpad form the layer structure to make up a touchscreen, the display unit 310 may also be used as an input device, other than an output device. When the display unit 310 includes the touchscreen, examples of the touchscreen may include a touchscreen panel and a touchscreen panel controller.

In addition, the display unit 310 may include at least one of a liquid crystal display, a thin film transistor-liquid crystal display, an organic light-emitting diode, a flexible display, and a 3D display. Two or more display units 310 may also be provided according to types of the wearable device. For example, the wearable device may include an external display unit 310 and an internal display unit 310 simultaneously.

The display unit 310 may be implemented as a head-up display (HUD) or a head-mounted display (HMD). The HMD is an image display device that the user may wear on his or her head as glasses to enjoy a large-scale image. The HUD is an image display device that may project a virtual image onto a clear panel within the user's field of view.

The audio output module 320 may output audio data, received from the wireless communications unit or stored in the memory 260, in a call reception mode, the call mode or the recording mode, the voice recognition mode, and a broadcast reception mode. Further, the audio output module 320 may perform a function of the wearable device, for example, outputting an audio signal associated with a call ringtone or a message ringtone. The audio output module 320 may include a speaker or a buzzer.

The alarm unit 330 may output a signal for providing a notification of an occurrence of an event by the wearable device. Examples of the event, generated by the wearable device, may include call signal reception, message reception, or key signal input. The alarm unit 330 may output the signal for providing a notification of an occurrence of an event in format different from an audio signal or a video signal. For example, the alarm unit 330 may include a vibration alarm unit to output a signal in a vibration manner. When a call signal or a message is received in the wearable device, the alarm unit 330 may output a signal for providing a notification of the received call signal or message. Further, when a key signal is input to the wearable device, the alarm unit 330 may output a signal as feedback on the input of the key signal. The signal, output by the alarm unit 330, may enable the user to recognize an occurrence of an event. The wearable device may also output a signal for providing a notification of an occurrence of an event through the display unit 310 or the audio output module.

The haptic module 340 may create various haptic effects that the user may feel. A typical example of the various haptic effects, created by the haptic module 340, may include a vibration effect. When the haptic module 340 generates a vibration as a haptic effect, the haptic module 340 may change the strength and pattern of the vibration, and may also combine and output different vibrations, or sequentially output different vibrations.

The wireless communications unit 250 may include a broadcast reception module, a mobile communications module, a wireless Internet module, a short-range communications module, or a GPS module.

The broadcast reception module may receive at least one of a broadcast signal and broadcast-related information from an external broadcast management server through a broadcast channel. Here, the broadcast channel may include a satellite channel and a terrestrial channel. The external broadcast management server may refer to a server generating and transmitting at least one of a broadcast signal and broadcast-related information, or a server receiving at least one of a previously generated broadcast signal and broadcast-related information and transmitting the received at least one of a previously generated broadcast signal and broadcast-related information to a terminal.

The broadcast-related information may refer to information related to a broadcast channel, a broadcast program, or a broadcast service provider. The broadcast-related information may also be provided through a mobile communications network. In this case, the broadcast-related information may be received by the mobile communications module. The broadcast-related information may exist in various forms.

The broadcast reception module may receive the broadcast signal using various types of broadcast systems, and may receive a digital broadcast signal using a digital broadcast system. Further, the broadcast reception module may be suitable to all broadcast systems that provide the broadcast signal, as well as to such a digital broadcast system. The broadcast signal and/or the broadcast-related information, received by the broadcast reception module, may be stored in the memory 260.

The mobile communications module may transmit a wireless signal to, and receive a wireless signal, from at least one of a base station, an external terminal, and a server on the mobile communications network. Here, the wireless signal may include a voice call signal, a video call signal, or various types of data, according to a text or multimedia messaging service (MMS) message.

The wireless Internet module may refer to a module for access to wireless Internet, and may be embedded in, or out of, the wearable device. Examples of a wireless Internet technology may include wireless local area network (WLAN) (Wi-Fi), WiBro, worldwide interoperability for microwave access (WiMAX), HSDPA, LTE, and LTE-A.

A short-range communications module 116 may refer to a module for short-range communications, as mentioned above in FIG. 1. Examples of a short-range communications technology may include Bluetooth®, RFID, IrDA, UWB, Zigbee®, and Z-wave.

In an exemplary embodiment in the present disclosure, the beacon as a wireless communications device may transmit a signal, having a significantly low frequency, therearound, using a Bluetooth® v. 4.2 BLE-based protocol. Bluetooth® v. 4.2 may enable the wearable device to communicate with devices within an about 100 m radius of the wearable device, and may consume less power to hardly affect the battery life to significantly reduce wastage of power, thus seamlessly being activated.

Further, Bluetooth® v. 4.2 may enable a Bluetooth® sensor or devices to directly access the Internet with the development of Internet protocol support profile (IPSP). In addition, IPSP may enable an unlimited Internet address system, IPv6, and IPv6 over low power wireless personal area networks (6LoWPAN), a low-power wireless communications technology, to apply to Bluetooth®.

Moreover, Bluetooth® v. 4.2 may increase security through supporting of 128-bit advanced encryption standard (AES) encryption, increase its data rate by 2.5 times or more through increasing of the packet capacity between devices, and further enhance power consumption efficiency.

Depending on the above-mentioned features, Bluetooth® v. 4.2 may enable a Bluetooth® sensor or device to directly access the Internet, so that the user may transmit Bluetooth® information to a cloud application without a smartphone application and may also view the Bluetooth® information on a web browser.

The GPS module 115 may receive position information from a plurality of GPS satellites, and may measure the current position of the user using the received position information.

The memory 260, a storage unit, or a memory unit may store a program for processing and control of the control unit 210, and may also perform a function of temporarily storing pieces of data (for example, a message, a still image, and a video) to be input or output.

The memory 260 may include at least one type of storage medium among a flash memory 260-type memory, a hard disk-type memory, a multimediacard micro (MMCmicro)-type memory, a card-type memory (for example, a secure digital (SD) or xD-picture (XD) memory), and a random access memory (RAM). Further, the wearable device may also operate a web storage that performs a storage function of the memory 260 on the Internet.

The interface unit 270 may interface with all external devices connected to the wearable device. Examples of the external devices, connected to the wearable device, may include a wired/wireless headset, an external charger, a wired/wireless data port, a memory card, a card socket such as a subscriber identification module (SIM) or a user identity module (UIM), an audio input/output (I/O) terminal, a video I/O terminal, and an earphone. The interface unit 270 may receive data or power from such external devices, may transmit the received data or power to the respective components of the wearable device, and may allow data, stored in the wearable device, to be transmitted to the external devices.

The control unit 210 or an information processing module may function to control the overall operation of the wearable device by commonly controlling operations of the respective components. For example, the control unit 210 may perform control and processing related to a voice call, data communications, or a video call. Further, the control unit 210 may function to process data for multimedia playback. In addition, the control unit 210 may function to process data received from the input unit or the sensing unit 130.

The context evaluation module 230 may function to determine a context in which the user uses the wearable device, based on criteria stored in the memory 260 or on those received from the user. That is, the context evaluation module 230 may function to configure the wearable device or to determine a signal to be received by determining the context in which the user uses the wearable device, based on various criteria.

The voice recognition unit 220 may function to identify the contents of semantic meaning from voice by an automatic means. In detail, this function may be a process of inputting a voice waveform, identifying a word or a word string therefrom, and extracting a meaning therefrom, which may largely be divided into five categories: voice analysis, phoneme recognition, word recognition, sentence interpretation, and semantic extraction. The voice recognition unit 220 may further include a voice evaluation module that compares whether a stored voice is the same as an input voice. In addition, the voice recognition unit 220 may further include a voice-text conversion module 240 that converts an input voice into text, or text into voice.

The power supply unit may receive power from an external or internal power source under the control of the control unit 210, and may supply power required for operations of the respective components.

Hereinafter, a wearable device for generating an image signal according to exemplary embodiments in the present disclosure, and a system for controlling the same will be described with reference to the drawings.

Figure 3:
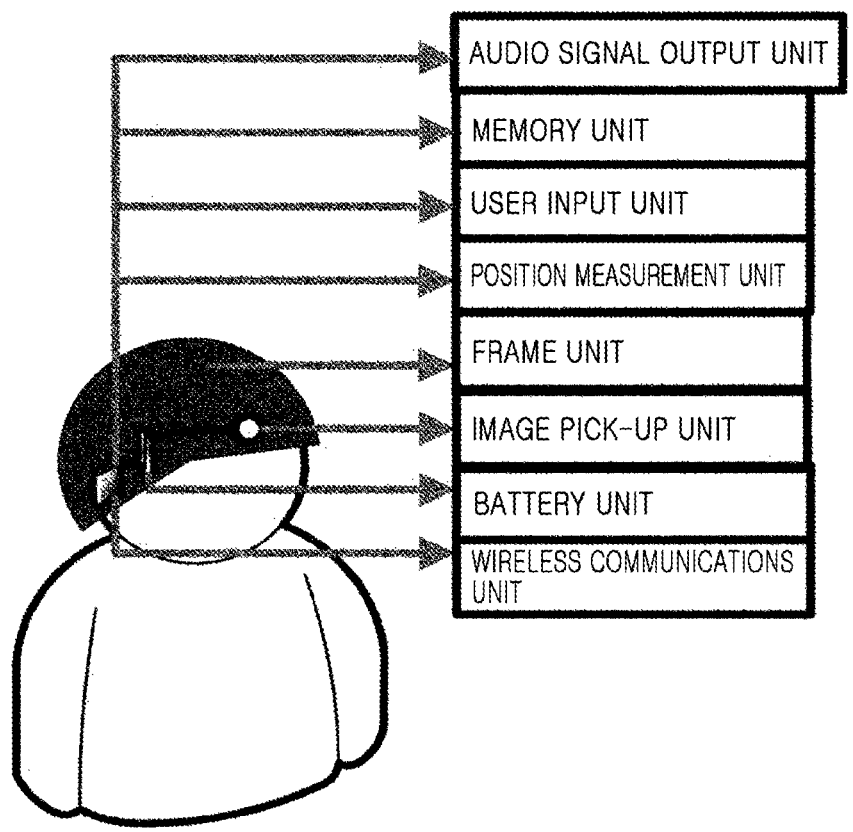
FIG. 3 is a diagram illustrating a wearable device generating an image signal according to an exemplary embodiment in the present disclosure.

FIG. 3 is a diagram illustrating a wearable device generating an image signal according to an exemplary embodiment in the present disclosure.

Referring to FIG. 3, an image signal generation device, according to an exemplary embodiment in the present disclosure, may be implemented as a wearable device, having the concept of the IoT device mentioned above in FIG. 2, and accordingly, the image signal generation device may be implemented to include the features of the respective components stated in the description of the wearable device of FIG. 2, even without an additional explanation in FIG. 3.

The image signal generation device 100 may include a frame unit, an image pick-up unit, a battery unit, a wireless communications unit, and a control unit. According to an exemplary embodiment in the present disclosure, the image signal generation device may include or may not include components such as a voice signal output unit, a user input unit, and a position measurement unit. In contrast, the image signal generation device may further include another component included in the wearable device mentioned above in FIG. 2.

Meanwhile, the respective components, included in the image signal generation device of FIG. 3, may perform the same functions as the components included in the wearable device described above in FIG. 2. In an exemplary embodiment in the present disclosure, the image signal generation device may be interpreted as further including a device that may capture a surroundings image, transmit the captured image to a biometric state measurement device and a server, and receive a response to the transmitted captured image therefrom.

In an exemplary embodiment in the present disclosure, the frame unit may be a helmet wearable on the head of the user. As described above, when the frame unit of the wearable device is implemented in helmet form, a user surroundings image, captured by the image pick-up unit included in the wearable device, may be captured from a location of the helmet. Thus, the user surroundings image may be captured from the same point of view as that of the user wearing the helmet.

As a result, according to an exemplary embodiment in the present disclosure, an image, captured from the same point of view as that of the user wearing the helmet, may be generated and provided to the user. When an external device receives the captured image from the wearable device and displays the image, an observer of the external device may observe surroundings of the user from the same point of view as the wearable device's user, even in a remote location. Further, the head of the user, on which the wearable device is worn, may shake relatively less, and when worn on the head of the user, the wearable device may capture an image in a consistent direction, compared to when worn on the wrist, the arms, the body, or the legs of the user. According to an exemplary embodiment in the present disclosure, when the frame unit of the image signal generation device is implemented as the helmet wearable on the head of the user, a captured image may be prevented from being wasted due to a frequent movement of the head.

Figure 4:
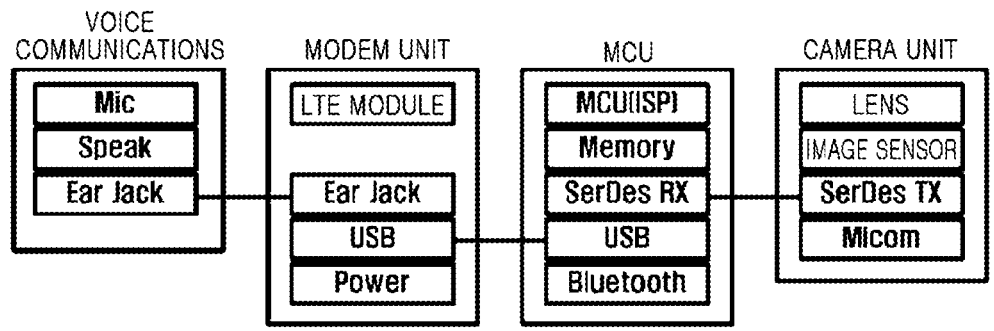
FIG. 4 is a block diagram illustrating the configuration of a wearable device generating an image signal according to an exemplary embodiment in the present disclosure.

Meanwhile, according to an exemplary embodiment in the present disclosure, the image signal generation device may receive an alarm signal from the biometric state measurement device. Here, the alarm signal may refer to a signal transmitted in the case that, when a value, represented by a biometric signal of the biometric state measurement device's user, is compared with a value, represented by an existing biometric state result received from the external device, or with a predetermined reference value, the values differ from each other by an amount equal to the predetermined value or more. The image signal generation device may capture a user surroundings image, using a camera included in the image pick-up unit, in response to the reception of the alarm signal. The image pick-up unit (or a camera unit) may include, as illustrated in FIG. 4, a lens used for image capturing, an image sensor, a serializer/deserializer (SerDes) transmitter (TX) used to transmit a captured image, and a microcomputer (MICOM), a processor controlling the image pick-up unit. The image pick-up unit may further capture at least one of a lateral image and a rear image, as well as a front image, when capturing the user surroundings image using the camera, and may include audio, audio information, other than a video image, visual information, when capturing the above images.

Further, the image signal generation device may include the position measurement unit, which may measure a position of the image signal generation device's user, using the GPS or BLE, under the control of the control unit.

In more detail, when a device exists, transmitting a beacon usable to measure a position in any space or building in which various kinds of disaster, including a fire, may occur, the image signal generation device may connect to the device to receive the beacon from the device, and may measure the position of the user wearing the image signal generation device by transmitting position information thereof to a predetermined external device, based on the received beacon.

Furthermore, the measuring of the position of the user wearing the image signal generation device may also be performed by the image signal generation device itself using the GPS and the camera.

As described above, as it is possible to measure the position of the user wearing the image signal generation device, a person in a remote location may be able to determine the current position of the user wearing the image signal generation device, as well as help the image signal generation device's user to move accurately quickly by transmitting route information to the image signal generation device or transmitting and receiving a voice signal through a voice communications unit (or the voice signal output unit) included in the image signal generation device, as illustrated in FIG. 4.

Meanwhile, the image signal generation device that has performed the surroundings image capturing or the position measurement may generate an image signal, including the captured image, or user position measurement information, including user position information, and may transmit the generated image signal and user position measurement information to the external device (for example, all devices, such as a PC, a smartphone, or a server, connectable to the image signal generation device through wired and wireless communications) through the wireless communications unit (or a modem unit) of the image signal generation device illustrated in FIGS. 3 and 4. The above transmission may be performed using a short-range communications module, using a scheme such as Bluetooth® or the like, or using a wireless Internet module, including an LTE module.

As previously mentioned, according to an exemplary embodiment in the present disclosure, when the image signal generation device includes an LTE communications module for transmitting a communications signal to, and receiving a communications signal from, at least one external device, the image signal generation device may be connected to the external device (for example, the server or the remote monitoring device) in a remote location through the LTE communications module in real time, and may further transmit a communications signal to, and receive a communications signal from, the external device through the LTE communications module.

Thus, according to an exemplary embodiment in the present disclosure, since the image signal generation device may transmit the communications signal to, and receive the communications signal from, the external device in a relatively wider range, compared to the short-range communications module (for example, a Zigbee® or Bluetooth® communications module) that may transmit and receive a communications signal only within a predetermined short range, the wearable device, according to an exemplary embodiment in the present disclosure, that reduces restrictions on the transmission and reception range may be very useful in an emergency situation, such as a fire or disaster, that frequently requires long-range communications.

Further, upon transmitting the communications signal, the image signal generation device may directly transmit the communications signal to the external device, or may also transmit the communications signal to the external device through a relay station within a predetermined radius of the user.

Here, the relay station may refer to a small cell for low power/short-range communications, for example, a pico cell or a femto cell. Merely, at the scene of a fire, all fixed relay stations, as described above, may be destroyed by the fire, and thus the relay station may include a small device, having mobility, (for example, a relay station attached to a ladder truck located outside a building in which a fire has occurred, or a mobile relay station (a small cell) implemented to be suitable for a firefighter to throw when entering the building to extinguish a fire.

Further, the captured image and the user position measurement information may be stored in the memory unit or the memory for performing a storage function within the image signal generation device, and the transmitting and the storing may be performed simultaneously or individually.

Moreover, the image signal generation device may further include a wireless communications unit (a communications modem) used to transmit the captured image or the like, and the wireless communications unit may be detachably attached inside or outside the image signal generation device. Further, the wireless communications unit may further include a battery to further reduce power consumption of the image signal generation device, and the battery may also be included in the image signal generation device.

At this time, the battery may be implemented as a lithium-ion battery, using a liquid electrolyte and having a high level of energy storage density, a lithium-ion polymer battery, using a solid- or gel-polymer as an electrolyte and having a light weight, a low level of internal resistance, and heat resistance, as well as a high level of energy storage density, thus achieving a high level of stability, or a lithium iron phosphate (LiFePO4) battery, having a structure in which phosphorus and oxygen are tightly bonded to prevent oxygen from being generated at high temperatures, thus being safe from a fire and explosion. However, this is only an example, and the battery may be implemented using all batteries, having been developed up to date or which will be developed in the future.

Further, the battery may be implemented as an ultra small, ultra slim, or flexible battery, and may be charged using a wireless charging technology using any one of a magnetic induction method and a magnetic resonance method.

Here, the magnetic induction method may enable a power source to supply power to a power destination in a short location using magnetic field resonance, and may refer to a method of charging the battery of the image signal generation device by an amount equal to power consumed, when the image signal generation device and a charger face each other at a predetermined distance. For example, in the case that the charger is installed together with the image signal generation device in a place in which the image signal generation device is stored, when the image signal generation device is stored in the place when not in use, or placed on the charger, the image signal generation device and the charger may maintain a predetermined distance therebetween, so that the battery of the image signal generation device may be charged by an amount equal to an amount of power consumed.

Further, the magnetic resonance method may enable a power source to wirelessly supply power to a power destination in a remote location using an internal coil, and may be a method capable of supplying power to a relatively remote distance, compared to the magnetic induction method.

Meanwhile, according to another exemplary embodiment in the present disclosure, the image signal generation device may perform or control the image capturing, the position measurement, the storing of the image signal, including the captured image, and the user position measurement information, including the position information, in the memory unit or the transmitting of the image signal and the user position measurement information to the external device, not by the alarm signal received from the biometric state measurement device, but by the user's instruction input through the user input unit.

Further, the biometric state measurement device, according to an exemplary embodiment in the present invention, may be implemented as a helmet-type wearable device, a glasses-type wearable device, an external remote controller, a bracelet, or a ring. However, these are only examples, and the biometric state measurement device may have any other form. Moreover, although not illustrated in FIG. 3, the image signal generation device may also be manufactured to include all configurations and operations of a biometric state measurement device to be described in FIG. 6 below.

Figure 5:
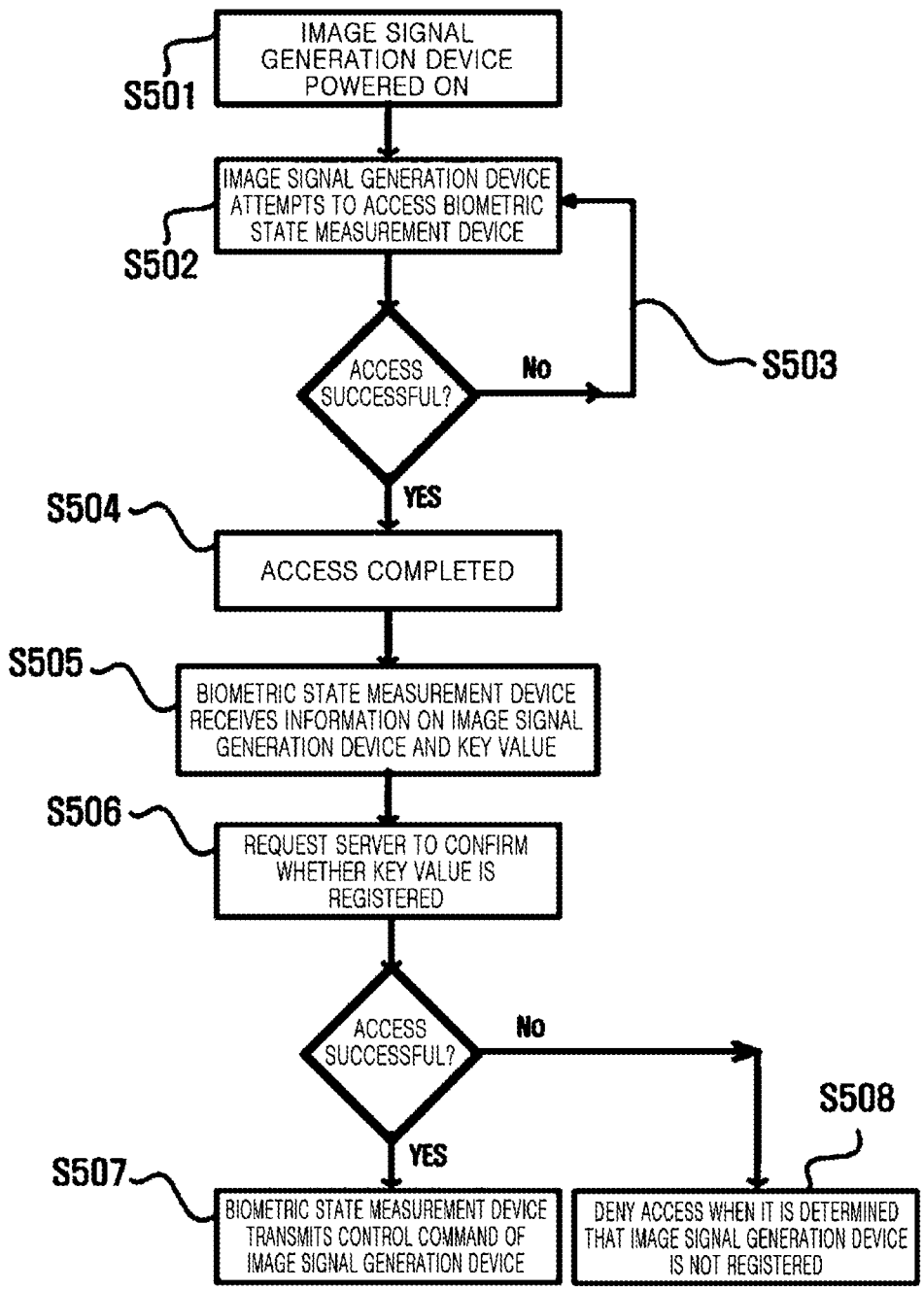
FIG. 5 is a flowchart illustrating a process of connecting a cell phone to a wearable device generating an image signal according to an exemplary embodiment in the present disclosure.

FIG. 5 is a flowchart illustrating a process of connecting a cell phone to a wearable device generating an image signal according to an exemplary embodiment in the present disclosure.

Referring to FIG. 5, when an image signal generation device is powered on to transition from an idle state to an active state, the image signal generation device may connect to (or access) other external device (for example, a biometric state measurement device or a cell phone) to transmit a captured image thereto (S501, S502). For convenience of explanation, the external device may be assumed to be a biometric state measurement device.

At this time, the connection may also be formed between the image signal generation device and the biometric state measurement device in a device-to-device (D2D) manner or by relay by a base station after a random access procedure on the base station.

In contrast, when the connection (access) fails, the image signal generation device may attempt to connect to the biometric state measurement device, according to settings, until the connection is successful (S503). When the connection (access) is successful (S504), the image signal generation device may transmit information on the image signal generation device and a key value to the biometric state measurement device (S505).

At this time, the key value may refer to a unique identification number of the image signal generation device, and may be previously stored in a related server. Thus, the biometric state measurement device that has received the key value from the image signal generation device may go through a procedure of confirming the key value of the image signal generation device through the server, and may connect to (access) the image signal generation device when the received key value matches the key value previously stored in the server, so that the image signal generation device may transmit the captured image to the biometric state measurement device or receive a control command from the biometric state measurement device (S506, S507).

When the key value, received from the image signal generation device, does not match the key value previously stored in the server, the biometric state measurement device may refuse to perform the connection (access), or may interrupt it (S506, S508).

Figure 6:
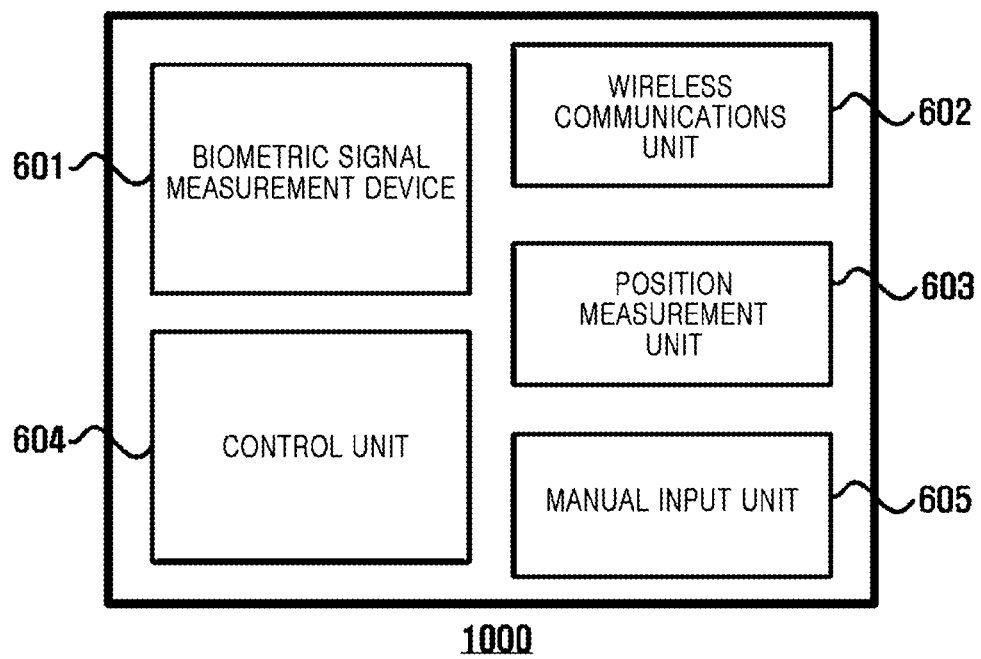
FIG. 6 is a block diagram illustrating a biometric state measurement device according to an exemplary embodiment in the present disclosure.

FIG. 6 is a block diagram illustrating a biometric state measurement device according to an exemplary embodiment in the present disclosure.

Referring to FIG. 6, the biometric state measurement device 200, according to an exemplary embodiment in the present disclosure, may be implemented as the wearable device described above in FIG. 2, and accordingly, may include the features of the respective components mentioned in the description of the wearable device.

The biometric state measurement device 200 may include a biometric signal measurement unit 601, a wireless communications unit 602, a position measurement unit 603, a control unit 604, and a manual input unit 605. Although not illustrated in FIG. 6, the biometric state measurement device 200 may further include a frame for wearing the biometric state measurement device 200 on the body of a user. Further, according to an exemplary embodiment in the present disclosure, the biometric state measurement device 200 may not include the above components, or may also include another component included in the wearable device described above in FIG. 2.

Meanwhile, the biometric signal measurement unit 601 of the biometric state measurement device 200 may sense or detect a user biometric signal, and for this purpose, may generate a sensing signal.

That is, the biometric state measurement device may be worn on the body of the user wearing the helmet to measure at least one type of biometric signal information among user heart rate, user body temperature, user skin condition, user body oxygen amount, user surroundings nitrogen amount, user surroundings carbon monoxide amount, and user surroundings ultraviolet light change.

Here, the user biometric signal may include user heart rate, user body temperature, user skin condition, user body oxygen amount, user surroundings nitrogen amount or user surroundings carbon monoxide amount, and user surroundings ultraviolet light change, and may further include all of the biometric signals that may be measured by the sensing unit 130, as mentioned above in FIG. 2.

Further, the biometric signal measurement unit may include all of a gyro sensor, an acceleration sensor, a proximity sensor, a pressure sensor, a motion sensor, a fingerprint recognition sensor, an iris recognition sensor, a heart rate sensor (a heart rate detector sensor), a body temperature sensor, a skin condition sensor (a skin temperature sensor), a skin resistance sensor, an ECG sensor, a UV sensor, and a body oxygen sensor (an oxygen amount sensor).

Figure 7:
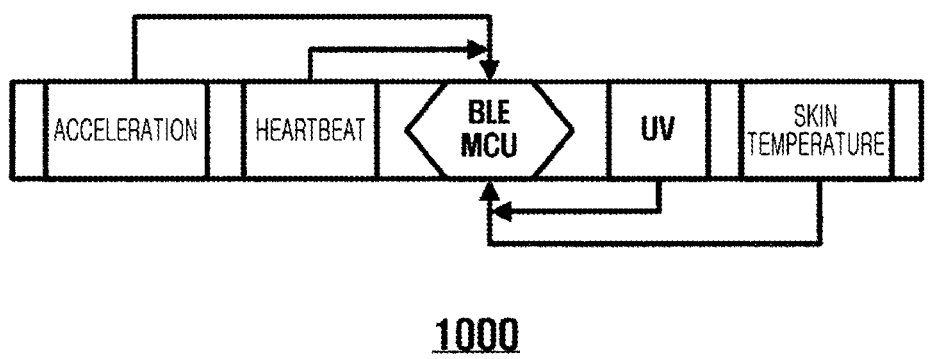
FIG. 7 is a block diagram illustrating the configuration of a biometric state measurement device according to an exemplary embodiment in the present disclosure.

For convenience of explanation, it is assumed that the biometric signal measurement unit includes, as illustrated in FIG. 7, a heart rate sensor, measuring a user heart rate, an acceleration sensor, measuring whether the user moves and a moving speed thereof, a body temperature sensor, measuring a user body temperature, a skin condition sensor, measuring a user skin condition, and a UV sensor, measuring a user surroundings ultraviolet light change.

Merely, the biometric signal measurement unit, illustrated in FIG. 7, may further include other sensors, such as an oxygen amount sensor, measuring a user body oxygen amount, a nitrogen amount sensor, measuring a nitrogen amount within a predetermined radius of the user, and a carbon monoxide amount sensor, measuring a carbon monoxide amount within a predetermined radius of the user, as mentioned above.

In an exemplary embodiment in the present disclosure, the biometric state measurement device 200 may measure the biometric signal of the user wearing the biometric state measurement device through the biometric signal measurement unit.

For example, when the user wearing the biometric state measurement device is exposed to the scene of a fire, the body temperature sensor of the biometric state measurement device may measure a change in a user body temperature due to heat generated by the fire, and the heart rate sensor may measure a change in a user heart rate, caused by the fire or the change in the user body temperature, by determining a change in a resistance value.

Further, when the user has difficulty in breathing due to smoke generated by the fire, so that the amount of oxygen present in the body of the user rapidly changes, the oxygen amount sensor may measure a change in the oxygen amount, and the UV sensor may measure a change in UV light around the user, using the method described above in FIG. 2, so as to detect whether the fire has occurred and the size of the fire.

For another example, when the user wearing the biometric state measurement device meets with an accident on a high, freezing mountain, the body temperature of the user may drop rapidly, and the body temperature sensor, measuring the user body temperature, may detect whether the user body temperature is changed with respect to a predetermined reference value and how much the user body temperature is changed, i.e., variation of the change.

Further, the skin condition measurement sensor included in the biometric state measurement device may also detect that the skin of the user is frostbitten due to a rapid drop in the user body temperature.

Meanwhile, the biometric state measurement device 200 may determine a user biometric state using the measured user biometric signal.

In more detail, according to an exemplary embodiment in the present disclosure, the biometric state measurement device may receive the existing biometric state result of the user from the external device, may compare the value, represented by the received existing biometric state result of the user, to the value, represented by the sensed user biometric signal, and may determine whether the value, represented by the sensed user biometric signal, differs from the value, represented by the received existing biometric state result, by an amount equal to the predetermined value or more, to determine the user biometric state.

Further, according to an another exemplary embodiment in the present disclosure, the biometric state measurement device may compare a reference value, preset by the biometric state measurement device itself, to the value, represented by the sensed user biometric signal, without using the existing biometric state result received from the external device as described above, and may determine whether the preset reference value differs from the value, represented by the sensed user biometric signal, by an amount equal to the predetermined value or more, to determine the user biometric state.

Here, the determining of the user biometric state may refer to a process of determining whether the user body temperature, the user heart rate, or the user skin condition that may be measured when the user is in a normal state has changed to the extent that user body temperature, the user heart rate, or the user skin condition reaches a predetermined risk level, according to changes in a user surroundings environment, and the determining of the user biometric state may be performed by the control unit of the biometric state measurement device.

Further, according to an exemplary embodiment in the present disclosure, when the biometric state measurement device includes a plurality of sensors, the biometric state measurement device may compare a biometric signal value, measured by at least one of the plurality of sensors, to the predetermined reference value, and may determine whether the measured biometric signal value differs from the predetermined reference value by an amount equal to the predetermined value or more. In contrast, when each of the plurality of sensors is previously prioritized, the biometric state measurement device may compare a biometric signal value, measured by a particular sensor having a high priority, of the plurality of sensors, to the predetermined value, and may determine whether the measured biometric signal value differs from the predetermined reference value by an amount equal to the predetermined value or more.

Meanwhile, the biometric state measurement device that has determined the user biometric state may generate an alarm signal, including the user biometric signal, in the case that the biometric state result has determined that the value, represented by the sensed or measured user biometric signal, differs from the value, represented by the existing biometric state result received from the external device, or the predetermined reference value, by an amount equal to the predetermined value or more, upon comparing the value, represented by the sensed or measured user biometric signal, to the value, represented by the existing biometric state result received from the external device, or the predetermined reference value.

The biometric state measurement device may transmit the generated alarm signal to the external device (for example, all devices connectable to the biometric state measurement device, such as a PC, a smartphone, or a server) through the wireless communications unit (or the communications modem). At this time, the transmitting may be performed using the short-range communications module or the wireless Internet module, particularly, a BLE module included in the biometric state measurement device.

Further, the biometric state measurement device may include the position measurement unit, which may measure a position of the biometric state measurement device's user using the GPS or BLE under the control of the control unit, and which may transmit the position measurement result to the external device through the wireless communications unit. The position measurement unit may perform the same function as the position measurement unit of the image signal generation device mentioned above in FIG. 3.

The alarm signal and the position information including the user biometric signal that have been transmitted to the external device through the above process may trigger capturing an image and transmitting the captured image by the image signal generation device according to an exemplary embodiment in the present disclosure, and may also be used to monitor or store the captured image and the position information on the external device.

Meanwhile, the sensing of the user biometric signal, the determining of the user biometric state, and the transmitting of the alarm signal may be controlled by the user, or may be remotely controlled by the external device connected to the biometric state measurement device, according to an exemplary embodiment in the present disclosure.

Meanwhile, the biometric state measurement device, according to an exemplary embodiment in the present disclosure, may be implemented as various forms such as a wristband-type wearable device or a glasses-type wearable device, an external remote controller, a bracelet, or a ring. However, this is only an example, and the biometric state measurement device may have any other form.

Figure 8:
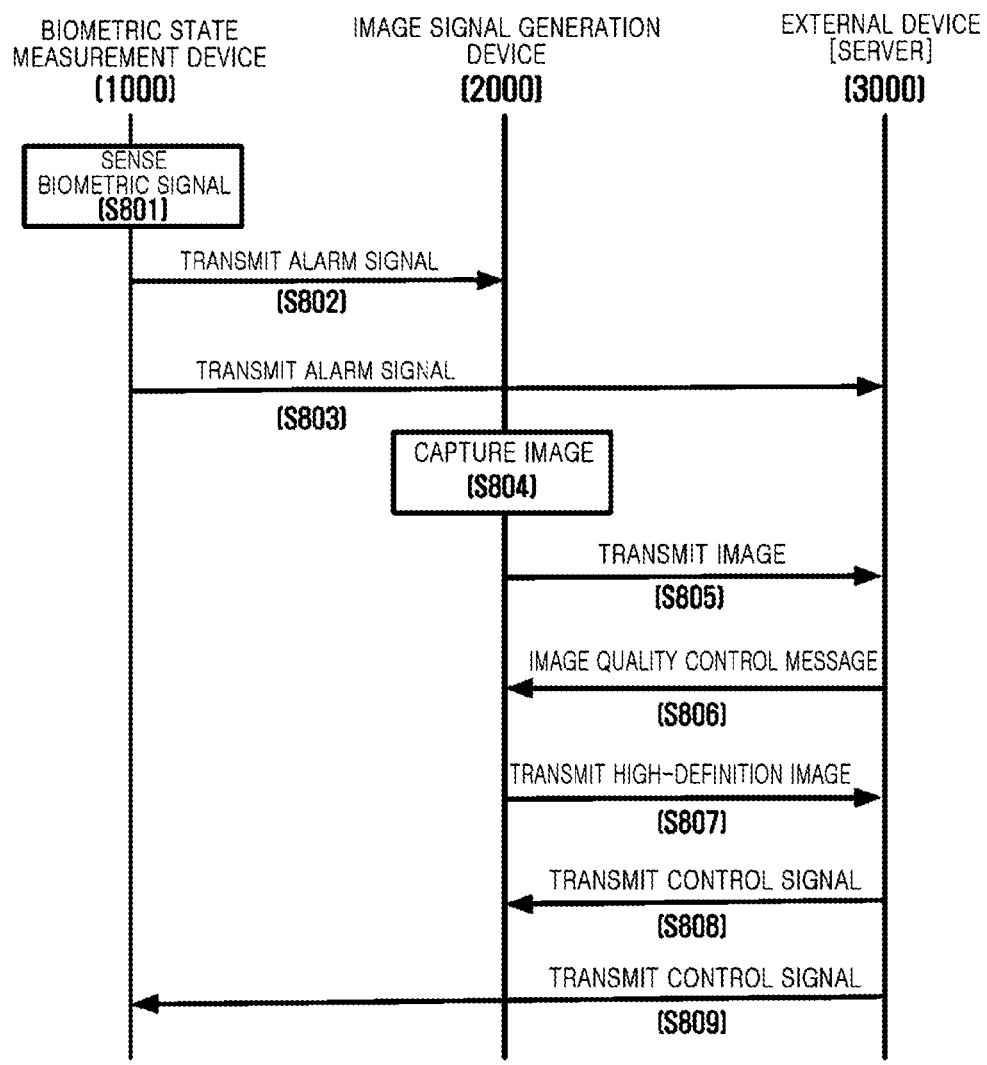
FIG. 8 is a flowchart illustrating a method of remotely monitoring a biometric state measurement device and a wearable device generating an image signal according to an exemplary embodiment in the present disclosure.

FIG. 8 is a flowchart illustrating a method of remotely monitoring a biometric state measurement device and a wearable device generating an image signal according to an exemplary embodiment in the present disclosure.

A system, remotely monitoring a physical condition, may include an image signal generation device 100, a biometric state measurement device 200, and a server 300. Here, the server 300 may refer to an external device or a device, such as a PC or a smartphone, that may be connected to the biometric state measurement device and the image signal generation device through wired and wireless communications.

The system, remotely monitoring a physical condition, will be detailed hereinafter, and descriptions of contents overlapping those described above will be omitted.

Meanwhile, the biometric state measurement device 200 may sense or measure a user biometric signal by the method mentioned above in FIG. 6 (S801). When comparing a value, represented by the user biometric signal, to a value, represented by an existing biometric state result received from the external device, in the case that the biometric state result is determined that the value, represented by the user biometric signal, differs from the value, represented by the existing biometric state result received from the external device, or a predetermined reference value, by an amount equal to the predetermined value or more, the biometric state measurement device 200 may transmit an alarm signal to the image signal generation device 100 and the server 300 (SS802, S803).

The server 300 that has received the alarm signal from the biometric state measurement device 200 may receive an image signal, including an image captured by the image signal generation device, from the image signal generation device, in response to an indication of the sensed biometric signal (S804, S805).

Further, although not illustrated in FIG. 8, the server 300 may also receive user position measurement information of the image signal generation device's user from the image signal generation device.

Meanwhile, according to an exemplary embodiment in the present disclosure, the server 300 that has received the image signal may transmit an image quality control message to the image signal generation device (S806), and may receive a captured image, having image quality of a predetermined standard or higher, from the image signal generation device, in response to the image quality control message (S807).

At this time, the image quality control message may refer to a message instructing the image signal generation device to interrupt the current image capturing thereof and to capture an image, having image quality of a predetermined standard or higher, from a point in time at which the image quality control message is received, and according to an exemplary embodiment in the present disclosure, the image quality control message may also include an instruction to adjust the frame rate, in addition to the instruction to control the image quality.

Further, the predetermined standard may be previously set as any one of image resolutions such as SD (D1(720×480), HD (1280×720), and full HD (1920×1080) and any one video codec compression method of MPEG-4, H.264, and H.265. However, this is only an example, and the predetermined standard may also be set as a different range of criteria.

Meanwhile, the server 300 that has received the user biometric signal and the image signal from the image signal generation device 100 and the biometric state measurement device 200 may divide and store the received user biometric signal and image signal by users, and may output the user biometric signal and the image signal through a display to monitor the user biometric signal and the image signal.

Further, the server 300 may compile statistics of the user biometric signal and the image signal, divided and stored by users, according to a preset method, and may output the statistical results through the display. The preset method may include all methods of compiling statistics of data.

Meanwhile, the server 300 that has received the image signal and the user position measurement information may transmit a control signal, including a control command, to the user of the biometric state measurement device and the image signal generation device, in consideration of a context based on the received image signal and user position measurement information, and the control signal may include a voice signal to be transmitted to the user, and the control command for controlling the biometric state measurement device and the image signal generation device (S808, S809).

Figure 9:
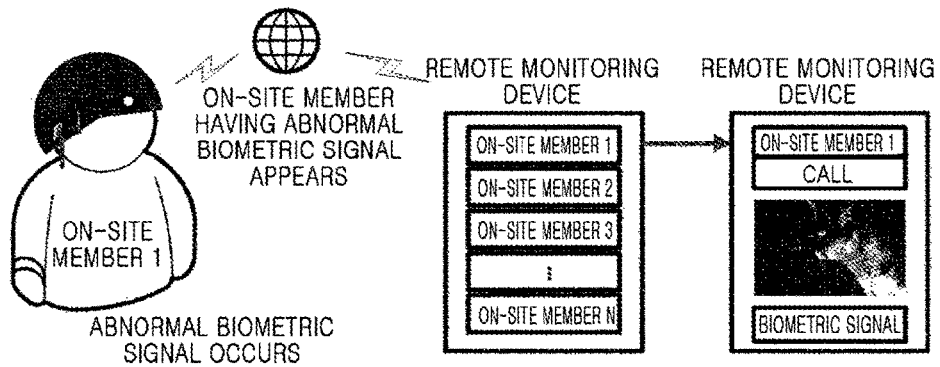
FIG. 9 is a diagram illustrating a method of remotely monitoring a biometric state measurement device and a wearable device generating an image signal according to an exemplary embodiment in the present disclosure.

FIG. 9 is a diagram illustrating a method of remotely monitoring a biometric state measurement device and a wearable device generating an image signal according to an exemplary embodiment in the present disclosure.

Referring to FIG. 9, assuming that a user, wearing a biometric state measurement device, is at the scene of a fire, or the like, when the user is injured by the fire, the biometric state measurement device, according to an exemplary embodiment in the present disclosure, may detect whether a user biometric state is abnormal, may generate an alarm signal according to the method described above in FIG. 6, and may transmit the generated alarm signal to an image signal generation device and a remote monitoring device, remotely monitoring or managing the context.

In response to the alarm signal, the image signal generation device may capture an image and may transmit the captured image to the remote monitoring device. Here, the image signal generation device may also transmit user position measurement information to the remote monitoring device, together with the captured image.

The remote monitoring device that has received the captured image and the user position measurement information from the image signal generation device may display the received captured image and user position measurement information in real time, and may store the above information.

Further, when there are a plurality of users of the image signal generation device transmitting the captured image and the user position measurement information, the remote monitoring device may divide and store or display the captured image and the user position measurement information by user. Accordingly, a user controlling the remote monitoring device may transmit a control signal, including a voice signal and a control command, to the image signal generation device's user.

Meanwhile, the user's biometric state measurement device and image signal generation device, according to an exemplary embodiment in the present disclosure, may measure the user position information, and may transmit the measured user position information to the remote monitoring server, respectively. Thus, the remote monitoring server that has received the user position information may generate information on a route along which the user is required to move, and may transmit the generated route information to the biometric state measurement device and/or the image signal generation device, respectively, so that the user may move based on the generated route information.

Further, the biometric state measurement device and the image signal generation device may compare the measured user position information to a preset user destination route (a route to a destination to which the user desires to move), and when the user's position and the preset user destination route do not match each other, each of the biometric state measurement device and/or the image signal generation device may generate an additional alarm signal and include information for notifying the user of such a fact in the generated alarm signal, or may include the information in an alarm signal to be transmitted to the remote monitoring server and transmit the alarm signal to the remote monitoring server.

Further, in contrast, the biometric state measurement device and the image signal generation device may compare the measured user position information to information on a preset area (a predetermined moving range within which the user is required to move), and when the user's position is outside of the preset area, each of the biometric state measurement device and/or the image signal generation device may generate an additional alarm signal and include information for notifying the user of such a fact in the generated alarm signal, or may include the information in an alarm signal to be transmitted to the remote monitoring server and transmit the alarm signal to the remote monitoring server.

Figure 10:
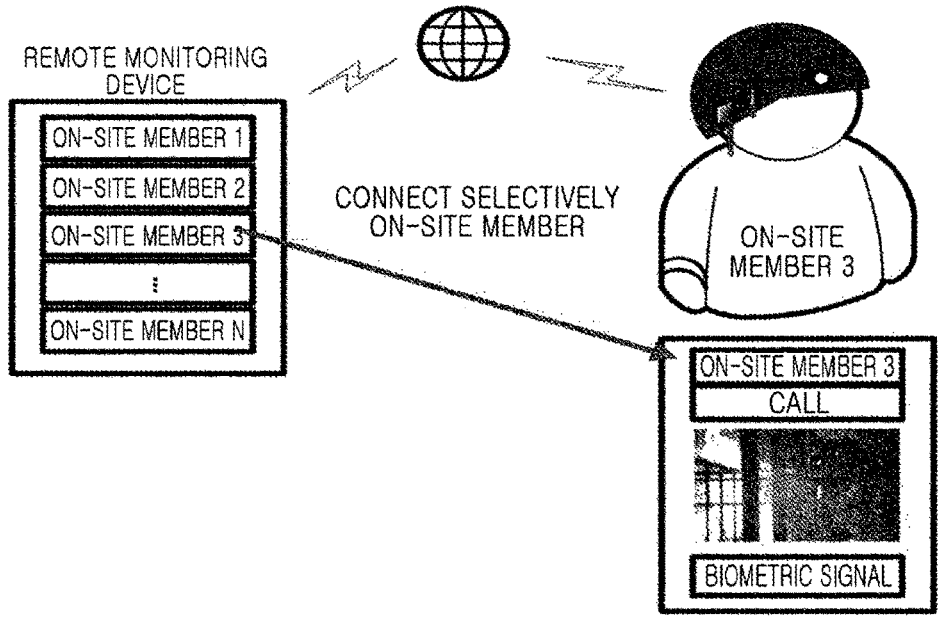
FIG. 10 is a diagram illustrating a method of remotely monitoring a biometric state measurement device and a wearable device generating an image signal according to another exemplary embodiment in the present disclosure.

FIG. 10 is a diagram illustrating a method of remotely monitoring a biometric state measurement device and a wearable device generating an image signal according to another exemplary embodiment in the present disclosure.

Referring to FIG. 10, when a remote monitoring device's user, remotely monitoring or managing context according to an exemplary embodiment in the present disclosure, desires to confirm surroundings and conditions of a user of an image signal generation device and a biometric state measurement device connected to the remote monitoring device, the remote monitoring device's user may transmit a control signal, requesting image information and biometric state information, to the image signal generation device and the biometric state measurement device.

At this time, when there are a plurality of users of the image signal generation device and the biometric state measurement device connected to the remote monitoring device, the control signal may be selectively transmitted only to any one of the image signal generation device and the biometric state measurement device, or may also be transmitted to all of the image signal generation device and the biometric state measurement device.

Accordingly, the image signal generation device and the biometric state measurement device that have received the control signal may capture a user surroundings image, generate user position measurement information, and measure a user biometric state, by the methods described above in FIGS. 3 through 8, and the image signal generation device and the biometric state measurement device may transmit the results to the remote monitoring device.

Accordingly, the user controlling the remote monitoring device may transmit the control signal, including a voice signal and a control command, to the image signal generation device's user, based on the received captured image, user position measurement information, and user biometric state measurement information.

Figure 11:
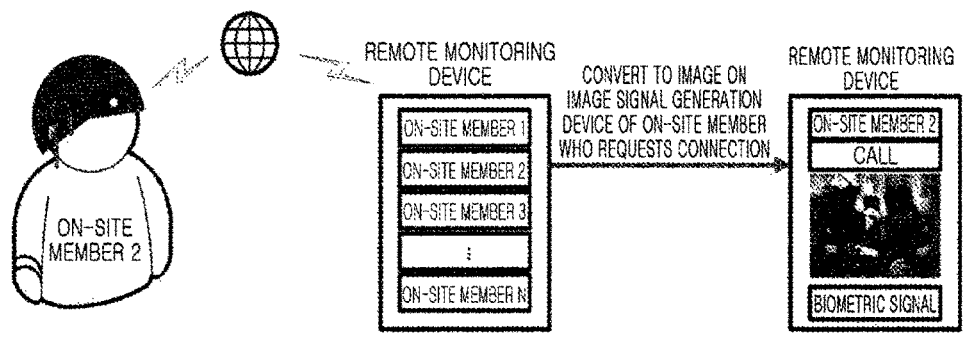
FIG. 11 is a diagram illustrating a method of remotely monitoring a biometric state measurement device and a wearable device generating an image signal according to another exemplary embodiment in the present disclosure.

FIG. 11 is a diagram illustrating a method of remotely monitoring a biometric state measurement device and a wearable device generating an image signal according to another exemplary embodiment in the present disclosure.

Referring to FIG. 11, according to an exemplary embodiment in the present disclosure, when a user of an image signal generation device and the biometric state measurement device desires to request a connection to a remote monitoring device's user, monitoring or managing context in a remote place, the user of the image signal generation device and the biometric state measurement device may input the above request through each user input unit of the image signal generation device and the biometric state measurement device. In this case, the user of the image signal generation device and the biometric state measurement device may call the remote monitoring device's user according to the above request.

In more detail, each of the image signal generation device and the biometric state measurement device may further include the user input unit, enabling the user to enter a control command, and may capture a user surroundings image and measure a position of the user, in response to the user's control command entered through the user input unit. In addition, each of the image signal generation device and the biometric state measurement device may perform at least one of storing the user surroundings image signal and the user position measurement information in a memory, and transmitting the user surroundings image signal and the user position measurement information to at least one external device.

Meanwhile, the user of the remote monitoring device that has received the request from the user of the image signal generation device and the biometric state measurement device may reply to the request, and when the remote monitoring device's user returns a connection acceptance response, a connection may be formed between the image signal generation device and/or the biometric state measurement device and the remote monitoring device.

At this time, when there are a plurality of users of image signal generation devices and biometric state measurement devices, there may be multiple requests, and when the remote monitoring device's user returns a connection acceptance response to all of the multiple requests, a connection may also be formed between the image signal generation device and/or the respective biometric state measurement devices and the respective remote monitoring devices.

Thereafter, the remote monitoring device's user may receive the captured image, the user position measurement information, or the like transmitted from the image signal generation device and the biometric state measurement device connected thereto, may confirm the received captured image, user position measurement information, or the like in real time in a remote place, and may transmit a control signal, including a voice signal and a control command, to the user of the image signal generation device and the biometric state measurement device, through a wireless communications network, based on the captured image, the user position measurement information, and the user biometric state measurement information.

In case of the implementation by firmware or software, one exemplary embodiment in the present disclosure may be implemented by modules, procedures, and/or functions for performing the above-described functions or operations.

Further, in the case of the implementation by hardware, one exemplary embodiment in the present disclosure may be implemented by one of application-specific integrated circuits (ASICs), digital signal processors (DSPs), digital signal processing devices (DSPDs), programmable logic devices (PLDs), field-programmable gate arrays (FPGAs), and the like installed in the control unit of the respective devices.

Meanwhile, the aforementioned method can be written as computer programs and can be implemented in general-use digital computers that execute the programs using a computer-readable recording medium. Further, a data structure used for the aforementioned method can be recorded by various means in a computer-readable media. Program storage devices usable for explaining a storage device, which includes an executable computer code configured to perform various methods of the present disclosure, should not be understood as a device including such temporary objects as carrier waves and signals. The computer-readable media includes such a storage media such as a magnetic storage media (e.g., a read only memory (ROM), a floppy disk, a hard disk, and the like) and an optical reading media (e.g., a compact disk-read only memory (CD-ROM), a digital versatile disc (DVD), and the like).

It will be apparent to those of ordinary skill in the art that various modifications and variations can be made therein without departing from the spirit and scope of the invention. The disclosed embodiments should be considered in a descriptive sense only and not for purposes of limitation. Thus, it is intended that the present disclosure covers the modifications and variations of this invention that come within the scope of the appended claims and their equivalents.

The invention claimed is:

1. A wearable device generating a user surroundings image signal in a wireless communications system, the wearable device comprising:
   a frame unit worn on a body of a user;
   an image pick-up unit capturing a user surroundings image;
   a battery unit supplying power to the wearable device;
   a Long-Term Evolution (LTE) communications module embedded in the wearable device, and directly connected to at least one external device to transmit and receive a communications signal;
   a voice signal input/output unit receiving a voice signal, to be transmitted to the at least one external device, from the user, or outputting a voice signal, received from the at least one external device, to the user; and
   a control unit controlling the image pick-up unit such that the image pick-up unit captures the user surroundings image in response to a first command received from a biometric state measurement device, the control unit controlling generating of a user surroundings image signal including the captured user surroundings image and transmitting of the generated user surroundings image signal to the at least one external device through the LTE communications module,
   wherein, when a value, represented by user biometric signal information measured by the biometric state measurement device, differs from a predetermined reference value by an amount equal to the predetermined value or more, the first command is transmitted from the biometric state measurement device.

2. The wearable device of claim 1, wherein the frame unit is a helmet wearable on the head of the user.

3. The wearable device of claim 2, wherein the biometric state measurement device is worn on the body of the user wearing the helmet to measure at least one type of biometric signal information among user heart rate, user body temperature, user skin condition, user body oxygen amount, user surroundings nitrogen amount, user surroundings carbon monoxide amount, and user surroundings ultraviolet light change.

4. The wearable device of claim 1, wherein the transmitting a signal to the at least one external device includes directly transmitting a signal to the at least one external device through the LTE communications module, or transmitting a signal to the at least one external device through a relay station within a predetermined radius of the user.

5. The wearable device of claim 3, wherein the first command includes the user biometric signal information measured by the biometric state measurement device, and when the value, represented by the measured user biometric signal information, differs from the predetermined reference value by an amount equal to the predetermined value or more, the first command is transmitted from the biometric state measurement device to the wearable device and the at least one external device, respectively.

6. The wearable device of claim 3, wherein the first command includes the user biometric signal information measured by the biometric state measurement device, and the first command receives existing biometric signal result information of the user from the at least one external device, compares a value, represented by the received existing biometric signal result information of the user, with the value, represented by the measured user biometric signal information, and when the value, represented by the measured user biometric signal information, differs from the value, represented by the received existing biometric signal result information, by an amount equal to the predetermined value or more, is transmitted from the biometric state measurement device to the wearable device and the at least one external device, respectively.

7. The wearable device of claim 1, wherein the battery unit includes any one of a lithium-ion battery, a lithium-ion polymer battery, or a lithium iron phosphate (LiFePo4) battery.

8. The wearable device of claim 1, further comprising a position measurement unit performing position measurement using global positioning system (GPS) or Bluetooth® low energy (BLE),
wherein the control unit controls the position measurement unit such that the position measurement unit measures a position of the user so as to generate user position measurement information.

9. The wearable device of claim 8, further comprising a memory unit storing the generated user surroundings image signal and the generated user position measurement information,
wherein the control unit controls storing the user surroundings image signal and the user position measurement information in the memory unit, or transmitting the user surroundings image signal and the user position measurement information to the at least one external device.

10. The wearable device of claim 9, further comprising a user input unit enabling the user to enter a control command,
wherein the control unit controls, in response to a second command entered through the user input unit, at least one of capturing a user surroundings image by the image pick-up unit, measuring a position of the user by the position measurement unit, storing the user surroundings image signal and the user position measurement information in the memory unit, and transmitting the user surroundings image signal and the user position measurement information to the at least one external device.

11. A device for measuring a user biometric signal in a wireless communications system, the device comprising:
a frame unit worn on the body of a user;
a biometric signal measurement unit sensing a user biometric signal;
an LTE communications module embedded in the device, and directly connected to at least one external device to transmit and receive a communications signal; and
a control unit determining a user biometric state by determining whether a value, represented by the sensed user biometric signal, differs from a predetermined reference value by an amount equal to the predetermined value or more,
wherein, when a biometric state result is determined as the value, represented by the sensed user biometric signal, differing from the predetermined reference value by an amount equal to the predetermined value or more, the control unit controls generating an alarm signal including the sensed user biometric signal and transmitting the generated alarm signal to a remote monitoring server through the LTE communications module, and the control unit transmits the generated alarm signal to an image signal generation device, wherein the alarm signal, transmitted to the image signal generation device, further includes image capturing instruction information for instructing the image signal generation device to capture a user surroundings image.

12. A system for remotely monitoring a physical condition using a wireless communications network, the system comprising:
an image signal generation device; a biometric signal measurement device; and
a remote monitoring server,
wherein, when as a sensing result of a user biometric signal, a biometric state result is determined as a value, represented by the sensed user biometric signal, differing from a predetermined reference value by an amount equal to the predetermined value or more, the biometric signal measurement device generates an alarm signal including the sensed user biometric signal and transmits the generated alarm signal to the remote monitoring server and the image signal generation device through an LTE communications module included in the biometric signal measurement device,
wherein the alarm signal, transmitted to the image signal generation device, further includes image capturing instruction information for instructing the image signal generation device to capture a user surroundings image, and
wherein the remote monitoring server is directly connected to the LTE communications module included in the biometric signal measurement device to receive the alarm signal including the user biometric signal, is directly connected to an LTE communications module included in the image signal generation device to receive an image signal including an image captured by the image signal generation device, and performs at least one of outputting the received captured image through a display unit or storing the received captured image in a memory.

13. The system of claim 12, wherein the remote monitoring server is any one of a personal computer (PC) or a user equipment (UE).

14. The system of claim 12, wherein the remote monitoring server transmits, to the image signal generation device, an image quality control message for instructing the image signal generation device to capture an image having image quality of a predetermined standard or higher, and in response to the image quality control message, receives, from the image signal generation device, a captured image having the image quality of the predetermined standard or higher.

15. The system of claim 12, wherein the remote monitoring server remotely connects to the biometric signal measurement device and the image signal generation device through the wireless communications network to control operations of the biometric signal measurement device and the image signal generation device.

16. The system of claim 12, wherein the remote monitoring server divides and stores, by users, the biometric signal, received from the biometric signal measurement device, and the captured image, received from the image signal generation device, and outputs the divided and stored biometric signal and captured image through a display according to previous division methods.

17. The system of claim 12, wherein the biometric signal measurement device and the image signal generation device are wearable devices able to measure a position of a user using a camera, GPS, and BLE, and the biometric signal measurement device and the image signal generation device transmit the measured user position information to the remote monitoring server, and receives, from the remote monitoring server, information on a route along which the user is required to move, based on the measured user position information.

18. The system of claim 14, wherein, when receiving the image quality control message for instructing the image signal generation device to capture the image having the image quality of the predetermined standard or higher, the image signal generation device captures an image, based on the image quality control message.

19. The system of claim 12, wherein, when a sensor included in the biometric signal measurement device includes a plurality of sensors, the system may compare a biometric signal value, measured by at least one of the plurality of sensors, with the predetermined reference value, so as to determine whether the measured biometric signal value differs from the predetermined reference value by an amount equal to the predetermined value or more.

* * * * *